United States Patent [19]

Fujiwara et al.

[11] 4,420,383
[45] Dec. 13, 1983

[54] FRACTIONATING METHOD IN ELECTROPHORESES

[75] Inventors: Toshihide Fujiwara, Hachiouji; Shinichi Kamachi, Hino, both of Japan

[73] Assignee: Olympus Optical Co., Ltd., Tokyo, Japan

[21] Appl. No.: 281,495

[22] Filed: Jul. 8, 1981

[30] Foreign Application Priority Data

Jul. 10, 1980 [JP] Japan ................................ 55-94161
Jul. 10, 1980 [JP] Japan ................................ 55-94162

[51] Int. Cl.³ ............................................ G01N 27/26
[52] U.S. Cl. ........................... 204/180 G; 204/180 S; 356/344; 356/444
[58] Field of Search ...................... 204/180 G, 180 S; 356/73, 344, 444

[56] References Cited

U.S. PATENT DOCUMENTS

4,118,781 10/1978 Brezinski et al. .................. 356/444
4,242,730 12/1980 Golias et al. ....................... 364/416
4,295,949 10/1981 Fujiwara et al. ............... 204/180 G
4,312,728 1/1982 Kamachi et al. ............... 204/180 G Primary Examiner—John F. Niebling
Attorney, Agent, or Firm—Cushman, Darby & Cushman

[57] ABSTRACT

A fractionating method in electrophoresis wherein, in order to make it possible to automatically and accurately fractionate a pattern obtained by the electrophoresis of a sample to be measured, respective peak tops or minimum points of the pattern obtained by electrophoresizing the sample to be measured are made to correspond to respective peak tops or minimum points to be obtained by electrophoresizing a normal sample by making the basic positions coincide with each other and the minimum points in the sample to be measured located in the positions nearest to the minimum points on the normal sample are made boundary points or the boundary points are determined on the basis of the ratios of the lengths from the basic position to the respective peak tops or minimum points in the sample to be meaured nearest to the values of the above mentioned ratios in the normal sample.

5 Claims, 18 Drawing Figures

FIG. 18

FRACTIONATING METHOD IN ELECTROPHORESES

BACKGROUND OF THE INVENTION (a) Field of the Invention

This invention relates to methods for treating fractionated patterns of serums formed by electrophoresis and more particularly to a method of determining respective boundary points of a fractionated pattern.

(b) Description of the Prior Art

Figure 1:
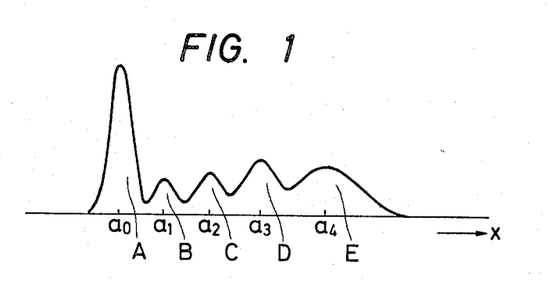
FIG. 1 is a diagram showing an electrophoretic pattern of a standard (reference) human serum.

FIG. 1 shows a basic pattern of concentration distribution on fractionated patterns formed by electrically energizing with an electrophoretic apparatus a carrier made of cellulose acetate film onto which man's serum is applied (a healthy man's serum generally shows this pattern). Such an electrophoretic patterns usually consists of five fractions of A, B, C, D and E including five peaks of $a_0$, $a_1$, $a_2$, $a_3$ and $a_4$ corresponding to albumin (A), $\alpha_1$ globulin (B), $\alpha_2$ globulin (C), $\beta$ globulin (D), and $\gamma$ globulin (E) respectively. Diagnosis or distinguishment between normality and abnormality is done on the basis of an analog diagram and values in percentage of the respective fractions. However, patterns of concentration distribution on fractionated patterns of actual sample to be examined may include peaks produced by various cases in addition to those shown in FIG. 1. The pattern illustrated in FIG. 2, for example, includes a peak designated as $a_5$ in addition to the five peaks mentioned above. This peak is produced due to turbidity in serum which allows a substance insensible of electrophoresis to remain at the position of sample application. The electrophoretic pattern shown in FIG. 3 includes an additional peak at the position of $a_6$, whereas the one shown in FIG. 4 includes an additional peak at the position of $a_7$. These peaks are produced by fractionation of certain components contained in the sera depending on their freshness, the additional peak shown in FIG. 3 being produced by $\beta$ lipoprotein and that in FIG. 4 being produced by $\beta_{1c}$ globulin.

Figures 5, 6:
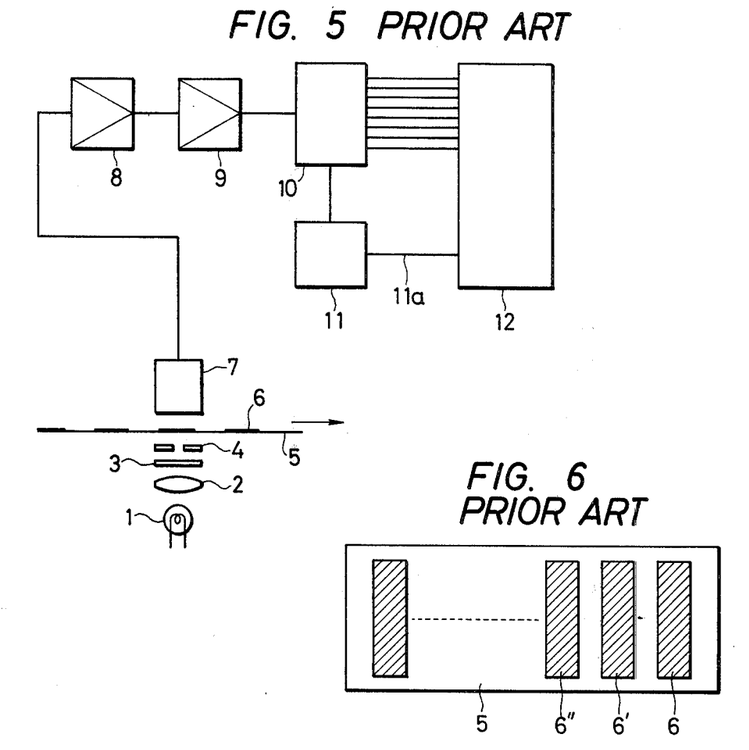
FIG. 5 is an explanatory view showing the formation of a generally used densitometer.
FIG. 6 is an explanatory view showing the arrangement of a sample to be examined on a carrier.

When colorimetry is done on a sample which shows peaks in addition to the five basic peaks, inconvenience is caused in automatic processing with a computer of data obtained by colorimetry. FIG. 5 shows an example of configuration of a densitometer and a photometric apparatus which are currently employed. In the block diagram shown in FIG. 5, the light emitted from a light source lamp 1 is passed through a lens 2, a filter 3 and a slit 4, used for irradiating a carrier 5 (described later) and detected with a photo detector element 7. The carrier 6 has fractionated patterns 6, 6', 6'',—of sera formed thereon as shown in FIG. 6, and is placed between the light source and the detector for photometry of the individual fractionated patterns 6, 6', 6'',—while scanning in the direction perpendicular to the shifting direction of the carrier 5. That is to say, the light emitted from the light source lamp 1 and passing through the sample (fractionated pattern or a serum) is received by the photo detector element 7, whose output corresponding to sample concentration is amplified with a preamplifier 8, converted by a logarithmic converter 9 into a logarithmic value and used for preparing an analog densitogram as shown in FIG. 1. Successively, output from the logarithmic converter 9 is inputted into an A/D converter 10 and converted into a digital signal by operating a conversion command signal generator 11 with a photometry command 11a from a computer 12. Value in percentage of each fraction is determined on the basis of the digital data obtained at this stage.

Figure 2:
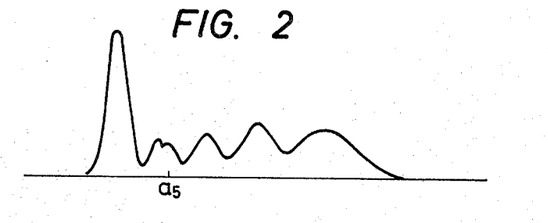
FIGS. 2 to 4 are diagrams showing electrophoretic patterns respectively including abnormal fractions.
Figure 3:
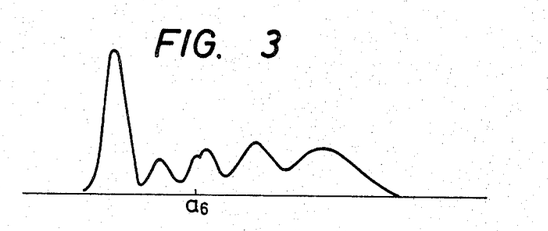
Figure 4:
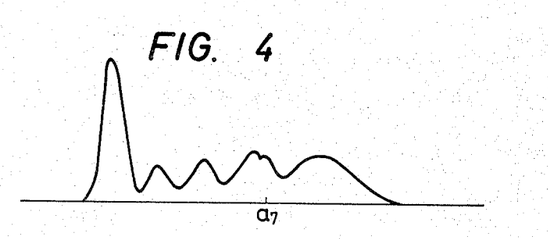

For the operations described above, it is sufficient to determine points of local minimum values as boundary points in such as case as shown in FIG. 1. In cases of the electrophoretic patterns divided into more than five fractions as illustrated in FIG. 2 through FIG. 4, however, it is impossible to determine values of the five fractions. In a case where an electrophoretic pattern has more than five fractions, it is therefore required for the analyst to check an analog pattern and electrophoretic pattern for recalculation through processing to attribute the additional peaks to any one of the areas corresponding to albumin, $\alpha_1$ globulin, $\alpha_2$ globulin and $\gamma$ globulin. In case of abnormal fractions due to disease, they may be reported with no attempt made for data processing.

A treating method wherein, under such circumstances as are described above, even in case an electrophoretic pattern is fractionated into six or more fractions, it will be able to be automatically rearranged as of normal five fractions by a computer is suggested by U.S. Pat. No. 4,295,949. This method (which shall be called the first conventional method hereinafter) shall be briefly explained as follows.

Figure 7:
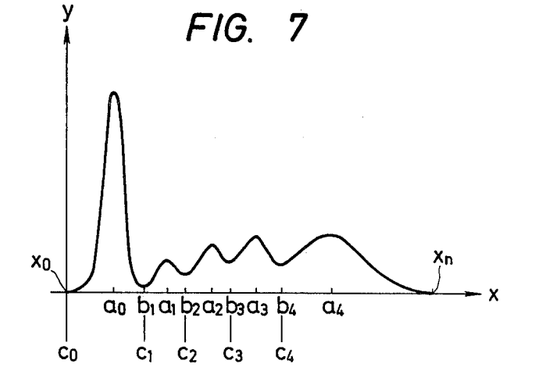
FIGS. 7 and 8 are electrophoretic pattern diagrams for explaining the first conventional method.

First, such serum to be a standard as is marketed is electrophoresizied as a control serum and is further measured with a densitometer to obtain an electrophoretic pattern of five fractions. The positions and boundary points of respective peaks of the electrophoretic pattern will be substantially determined by the kind of the carrier and the electrophoresizing conditions. Therefore, if the kind of the carrier and the electrophoresizing conditions are the same, the electrophoretic pattern of a serum to be tested will not be substantially different from that of the standard or normal serum. The standard lengths (from the basic point to the respective peak tops or boundary points) in the electrophoretic pattern of this standard serum are determined as follows. That is to say, such electrophoretic pattern of the standard serum as in FIG. 7 obtained as described above is sampled at fixed time intervals and is A/D-converted and the concentrations at the respective sampling points are memorized. In considering the axes x and y as shown in FIG. 7, it is found that the values of y at the respective sampling points on the axis x correspond to the concentrations (digital values) at the respective sampling points. On the basis of the concentrations at these respective sampling points, the detection of the respective boundary points shall be explained. As the respective boundary points are points on the axis x corresponding to the respective valley bottoms of the electrophoretic pattern, if any sampling point on the axis x is $x_b$ and the value of y at this sampling point is $y_b$ and, if the value of y at a sampling point $x_{b-1}$ is $y_{b-1}$ and the value of y at a sampling point $x_{b+1}$ is $y_{b+1}$, a sampling point $x_b$ having such values of $y_b$ as will satisfy the relations of $$y_b < y_{b-1} \text{ and } y_b < y_{b+1}$$

will be a boundary point. Next, the positions of peaks shall be described. There are respectively a peak top $a_0$ between the basic point $x_0$ and boundary point $b_1$, a peak top $a_1$ between the boundary points $b_1$ and $b_2$, a peak top $a_2$ between the boundary points $b_2$ and $b_3$, a peak top $a_3$ between the boundary points $b_3$ and $b_4$ and a peak top $a_4$ between the boundary point $b_4$ and end point $x_n$. These respective points satisfy the relations of $y_a > y_{a-1}$ and $y_a > y_{a+1}$. The positions of the thus determined points $b_1$, $b_2$,—and $a_0$, $a_1$,—are in proportional relations with the lengths on the axis x from the basic point to the respective points and correspond to 1:1. Therefore, these coordinates (in the fixed time intervals) may be used instead of the lengths from the basic point.

As in the above, the fractionation of the standard serum ends.

Figure 8A:
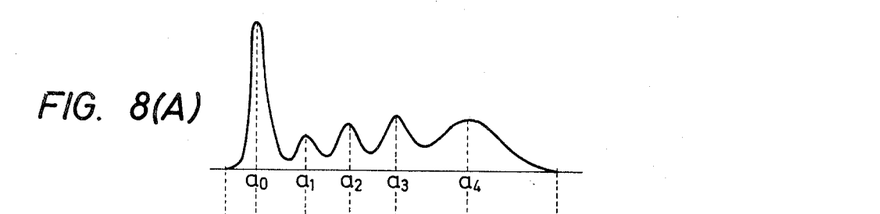
Figure 8B:
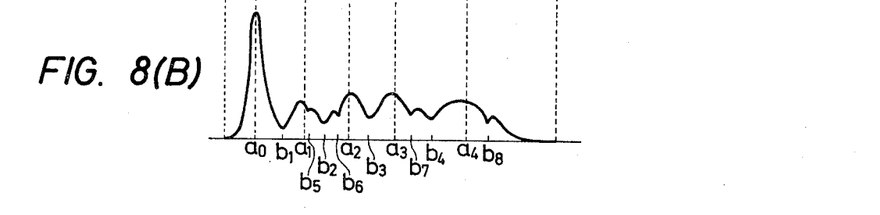

Then, boundary points are determined by using the above described method on a pattern obtained by electrophoresizing a sample to be measured. Then, with reference to the points $a_0$, $a_1$, $a_2$ and $a_3$ on the axis x corresponding to the respective peak tops in the electrophoretic pattern of the standard serum, these respective points are positioned on the axis x of the electrophoretic pattern of the sample to be measured as shown in FIG. 8. In the electrophoretic pattern of this sample to be measured, in case the number of the boundary points located in each of the sections between the points $a_0$ and $a_1$, between $a_1$ and $a_2$, between $a_2$ and $a_3$ and between $a_3$ and $a_4$ is counted and is 1, it will be made a boundary point. In case the number is 2 or more, the point of the smallest concentration or value of y will be made a boundary point and the others will be canceled. For example, in FIG. 8, as there is one boundary point ($b_1$ and $b_3$) in each of the sections between the points $a_0$ and $a_1$ and between the points $a_2$ and $a_3$, they will be respectively made the first boundary point and third boundary point, as there are three boundary points indicated by $b_5$, $b_2$ and $b_6$ between the points $a_1$ and $a_2$, the point $b_2$ having the smallest value among them will be made the second boundary point and, as there are two boundary points $b_7$ and $b_4$ between the points $a_3$ and $a_4$, the point $b_4$ of them will be made the fourth boundary point. The boundary point ($b_8$ in FIG. 8) further following the point $a_4$ will be all canceled. That is to say, the boundary points by $\beta$-lipoprotein, $\beta_{1c}$-protein and impurities always take values higher than those of normal five boundary points. Therefore, according to the above mentioned treating method, it is possible to make five boundary points.

The basic point is made the origin of the coordinates in the above explanation but the point $a_0$ corresponding to the first peak may be made the origin of the coordinates. However, in this first conventional method, a standard serum to be always normally fractionated is required. Some marketed standard serums are not always normally fractionated. It is thus difficult to select a standard serum. The sample to be examined will be influenced by the conditions of the place in which it is kept and will not be fractionated correctly into five fractions when it is polluted with bacteria. Therefore, it is a very difficult problem to keep a standard serum.

In order to solve such problem, there is recently suggested a fractionating method in electrophoresis wherein correct boundary positions are determined by utilizing the above described first conventional method and event without using a standard serum.

Figure 9:
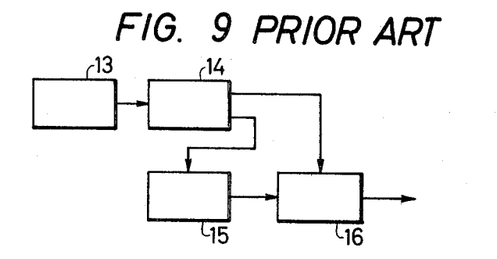
FIG. 9 is a block diagram of an apparatus for working the first conventional method.

This method (which shall be called the second conventional method herein-after) shall be explained in the following. FIG. 9 is a block diagram of a fractionating apparatus by utilizing the first method. An electrophoretic pattern of a standard serum is measured in a measuring device 13, the measured values are fractionated and judged by the above described method in a boundary position judging device 14 and the values ($a_0$, $a_1$, $a_2$, $a_3$ and $a_4$) of the coordinates x of respective peak points and the boundary positions ($b_1$, $b_2$, $b_3$ and $b_4$) are sent to and memorized in a basic position memorizing device 15. Then, an electrophoretic pattern of a sample to be examined is measured in the measuring device 13 and the values of the coordinates x corresponding to respective maximum values and minimum values are determined in the boundary position judging device 14 from the measured results. The thus determined values are compared with the values of the standard serum memorized in advance by a five-fraction treating device 16, correct boundary positions are determined by the already explained method and fractionated data are obtained on the basis of this fractionated data output.

In the second conventional method, the basic position is determined by the normally five-fractionated data of the sample to be examined without using a standard serum as in the first conventional method and is referred to in fractionating the sample to be measured into five fractions. It is known that the integrated values of the concentrations of the respective fractions, for example, of a normal human serum are in a fixed range. In the second conventional method, by noting this point, whether the fractions are normal or not is determined by whether the sample to be examined has five fractions and further the above mentioned integrated value of the concentration or the ratio of one fraction to the other fraction is in a fixed range or not, the basic position is determined on the basis of the fractions judged to be normal and the boundary positions of the sample to be examined are determined with reference to it.

Figure 10:
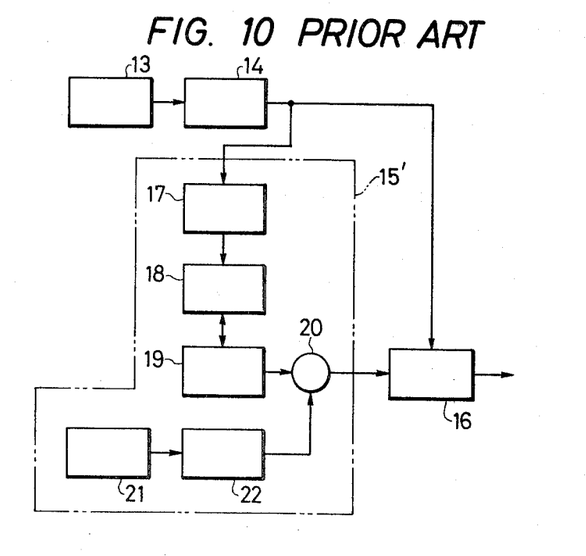
FIG. 10 is a block diagram for working the second conventional method.

Now, the second conventional method shall be explained on the basis of the block diagram in FIG. 10. The measured values of the sample to be examined are determined in the measuring device 13, the values of the coordinates x of the maximum values and minimum values of them are determined in the boundary position judging device 14 the same as in the case of FIG. 9. Then, whether the values determined in the boundary position judging device 14 have normal five fractions or not is judged in a normal fraction judging device 17. They have five fractions, the integrated values of the concentrations of the respective fractions fractionated by the respective valley bottom positions ($b_1$, $b_2$, $b_3$ and $b_4$) are determined and whether the fractions are normal or not is judged in the method by whether these integrated values are in the range set in advance or not. Only the data of the maximum values and minimum values judged to be normal in this normal fraction judging device 17 are sent to a next basic position calculating device 18 and a proper basic position is calculated by a proper statistical treatment. The basic position calculated here is sent to and memorized in a basic position memorizing device 19. The basic position memorized here corresponds to the basic position of the standard serum memorized in the basic position memorizing device 15 in the first conventional method (FIG. 9). Then the same as in the method of FIG. 9, the data from the boundary position judging device 14 of the sample to be examined are compared with the basic position memorized in the basic position memorizing device 19 and sent to the five-fraction treating device 16 through a switching device 20 and data fractionated with correct fractionated values are put out of the five-fraction treating device 16 and the integrated values of the concentrations of the respective fractions are calculated. Thus the basic position is determined by using the sample itself to be examined but without using the standard serum and is used to fractionate electrophoretic patterns of other samples to be examined. However, in the case of this second conventional method, though there is an advantage that it is not always necessary to use a standard serum, it has been still insufficient to properly fractionate the electrophoretic pattern of a sample to be examined into five fractions.

SUMMARY OF THE INVENTION

Therefore, a primary object of the present invention is to provide a method of automatically fractionating into more correct five fractions an electrophoretic pattern of a sample to be examined not normally fractionated.

According to the present invention, this object is attained by determining and memorizing, as reference positions, points on an abscissa corresponding to either of peak tops and minimum points on a densitogram obtained by electrophoresizing a reference humam serum sample; making to correspond the reference positions so as to have the same basic position on an abscissa of a densitogram obtained by electrophoresizing a human serum sample to be examined; comparing, the points on the abscissa corresponding to either of peak tops and minimum points on the densitogram obtained by electrophoresizing the human serum sample to be examined, with the reference positions corresponding to them; and treating only the points on the abscissa corresponding to the minimum points nearest to the reference positions as boundary points.

According to the feature of the present invention, the reference positions are treated as boundary points when the points on the abscissa corresponding to the minimum points nearest to the reference positions are not present in the above mentioned comparison step.

In the method according to the present invention, the basic position is selected to the point on the abscissa corresponding to a peak top of an albumin fraction or the starting position of the densitogram.

This and other objects of the present invention will become more apparent during the course of the following detailed description and appended claims.

DESCRIPTION OF THE PREFERRED EMBODIMENTS

Figure 11:
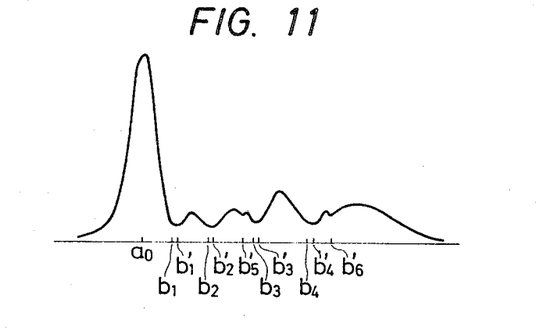
FIGS. 11 and 12 are electrophoretic pattern diagrams for explaining the first embodiment of the present invention.

First, the fractionating method according to the present invention shall be explained with reference to a human serum sample to be examined having such electrophoretic pattern (which is a densitogram obtained by an electrophoresis) as is shown in FIG. 11. In other words, a sample having more boundary points than the normal number.

In FIG. 11, a point $a_0$ on an abscissa corresponding to a peak top of an albumin fraction is selected as a basic point. Sampling points (on the abscissa) corresponding to respective minimum values are represented by reference symbols $b'_1$, $b'_2$, $b'_3$ and $b'_4$. In the case of this sample, minimum values by abnormal fractions are present and therefore the points on the abscissa corresponding to these minimum values are represented by reference symbols $b'_5$ and $b'_6$. Then, while the basic point $a_0$ is made to coincide on the abscissa of the electrophoretic pattern, the points (reference points) $b_1$, $b_2$, $b_3$ and $b_4$ on the abscissa corresponding to the respective minimum values in the electrophoretic pattern of the reference human serum sample (standard sample) are positioned. Next, the sampling points $b'_1$, $b'_2$, $b'_3$, $b'_4$, $b'_5$ and $b'_6$ are compared with the above mentioned respective reference points $b_1$, $b_2$, $b_3$ and $b_4$ and the sampling points located in the positions nearest to the respective reference points are determined to be boundary points. In FIG. 11, the sampling points near to the respective reference points are $b'_1$, $b'_2$, $b'_3$ and $b'_4$ but the other sampling points $b'_5$ and $b'_6$ are away from any reference positions and are therefore canceled. Thus the abnormal boundary points are canceled and correct five boundary points are determined.

Thus, in the sample to be examined having more than five fractions, the other boundary points than the normal boundary points are canceled. Therefore, even samples to be examined having such electrophoretic patterns as are shown in FIGS. 2 to 4 can be corrected fractionated.

Figure 12:
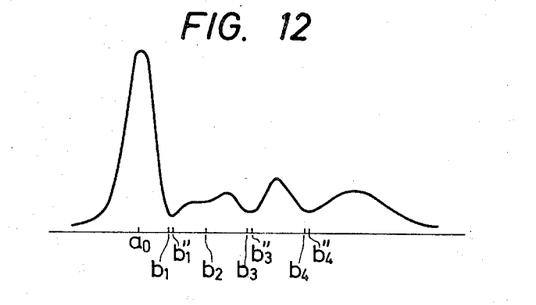

Now, such sample to be examined having less than four fractions as is shown in FIG. 12 shall be explained. In this case, too, as described above, points $b''_1$, $b''_3$ and $b''_4$ on the abscissa corresponding to respective minimum values are determined and reference positions $b_1$, $b_2$, $b_3$ and $b_4$ are made to correspond to them. Thus the minimum points located in the positions near to these reference positions are selected to be boundary points. In this case, no minimum value is present in the position near to the reference position $b_2$ but the position in the pattern corresponding to this reference position $b_2$ is added as a boundary point. Thereby, even in this case, the pattern can be fractionated into five fractions. Thus, though whether the newly added boundary point is proper or not is a problem, as a feature of the electrophoresis, if the treating time and conditions are fixed, the respective boundary points will be in substantially fixed positions. Therefore, if the electrophoretic pattern of the reference sample treated under the same treating conditions as for the sample to be treated is utilized, the boundary points selected as described above will be able to be considered to be in substantially correct position.

The above explained fractionating method can be automatically worked by a computer. That is to say, the positions of the points on the abscissa corresponding to the respective maximum values of the reference sample and the sample to be examined may be determined as values on the abscissa x by adopting the above mentioned first conventional method. Further, the method of making the reference positions correspond on the electrophoretic pattern of the sample to be examined can be attained by making the basic point (for example, the point on the abscissa x corresponding to the first peak) of the electrophoretic pattern of the sample to be examined coincide with the basic point (for example, the point on the abscissa x corresponding to the first peak) of the electrophoretic pattern of the reference sample. The method of selecting the normal boundary points among the positions on the abscissa x corresponding to the respective minimum points can be performed by respectively determining the differences between the values on the abscissa x of the respective minimum points of the electrophoretic pattern of the sample to be examined and the values on the abscissa of the respective reference positions and determining the minimum points in the electrophoretic pattern of the sample to be examined of the smallest differences in the respective reference positions. In the case of a sample to be examined having six or more fractions, incorrect boundary points will be always away from the reference positions as compared with the correct boundary points and therefore their differences will be larger than the differences of the correct boundary points from the reference positions. Therefore, the incorrect boundary points will never be determined to be boundary points. Further, in the case of four or less fractions, the difference of the boundary point from the reference position corresponding to a point not detected will be larger than the difference between the other reference position and the boundary point near to it and therefore the boundary point corresponding to that reference position will be immediately found not to be present. As a result, as described above, the basic position itself is added as a boundary point.

In the above explanation, the point on the abscissa x corresponding to the first peak value of the standard sample (albumin) and the point on the abscissa x corresponding to the first peak value of the sample to be examined were respectively selected to be basic points and were made to coincide with each other and then the pattern was fractionated.

Besides the above method, the starting position in the electrophoretic pattern of the sample to be examined may be selected to be a basic point. That is to say, in FIG. 7, a point $c_0$ may be selected to be the basic point, the values $c_1$, $c_2$, $c_3$ and $c_4$ on the abscissa x from it may be made values corresponding to the reference positions and minimum values and the pattern may be fractionated by the same method as is described above from the differences between the values $c_1$, $c_2$, $c_3$ and $c_4$ of the standard sample and the values of the sample to be examined.

In the above described method, whenever the pattern of each sample to be examined is fractionated, the reference positions will have to be determined by the standard sample. However, this method is made to attain the same object by a method quite different from the above mentioned first conventional method. Therefore, if the method of the present invention is applied as a means of fractionating the pattern of the sample in the first step part in the above mentioned second conventional method, the pattern of the examined sample will be able to be fractionated without light-measuring and fractionating the standard sample each time.

Some other embodiments of the present invention shall be explained in the following.

It is generally known that an electrophoretic pattern determined by a fractionated pattern obtained by electrophoresizing a serum protein takes a fixed form depending on the kind of the carrier. It is also known that, as described above, in the electrophoresis, even if such treating conditions as an electric current vary, the obtained electrophoretic patterns will be similar in the form to each other. Therefore, if the same kind of carrier is used, the ratios of the intervals between the peak points or minimum points corresponding to each other in different electrophoretic patterns will be equal. From such viewpoint, it is possible to determine normal boundary points by comparing the ratios of the lengths on the abscissa between the respective peak points or minimum points in the electrophoretic pattern of the sample to be examined with the ratios of the lengths on the abscissa between the respective peak points or minimum points in the electrophoretic pattern of the standard serum. The various embodiments explained in the following are of the fractionating method utilizing such feature.

Figure 13:
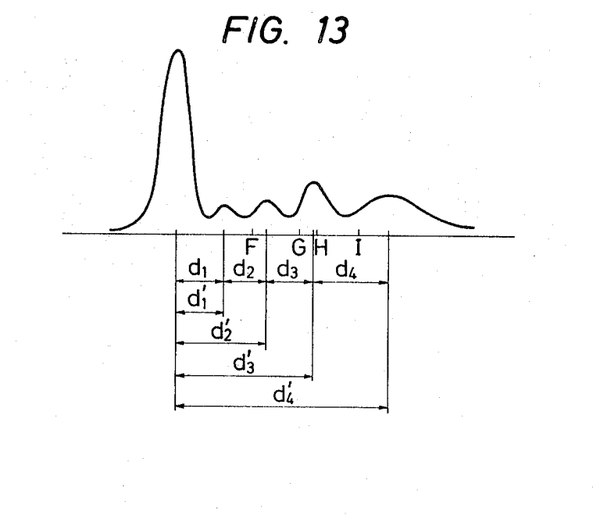
FIGS. 13 and 14 are electrophoretic pattern diagrams for explaining the second embodiment of the present invention.
Figure 14:
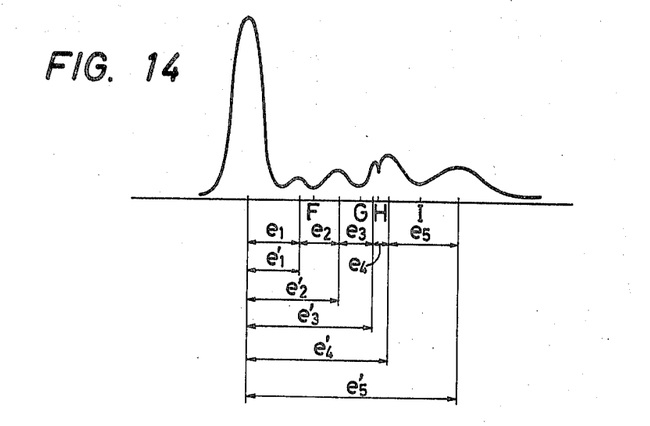

FIGS. 13 and 14 are diagrams for explaining the second embodiment of the present invention. In this embodiment, first such respective peak tops in the electrophoretic pattern of a standard sample as are shown in FIG. 11 are determined and the ratio of $d_1:d_2:d_3:d_4$ of the lengths $d_1$, $d_2$, $d_3$ and $d_4$ on the abscissa x corresponding to the sections between the respective peak tops is determined. Then such respective peak tops in the electrophoretic pattern of a sample to be examined as are shown in FIG. 14 are determined and the lengths $e_1$, $e_2$, $e_3$, $e_4$ and $e_5$ on the abscissa x corresponding to the sections between these respective peak tops are determined. The ratios in the following (1) to (4) are determined on the basis of these length values:

$$(e_1+e_2):e_3:e_4:e_5 \qquad (1)$$

$$e_1:(e_2+e_3):e_4:e_5 \qquad (2)$$

$$e_1:e_2:(e_3+e_4):e_5 \qquad (3)$$

$$e_1:e_2:e_3:(e_4+e_5) \qquad (4)$$

The ratio nearest to the ratio of $d_1:d_2:d_3:d_4$ of the standard sample is determined from among these ratios in (1) to (4) above. In the case of the illustrated example, the ratio in (3) above is found to be the nearest to that of the standard sample. Therefore, the lengths $e_3$ and $e_4$ should be naturally within one fraction and therefore the boundary point indicated by H corresponding to the minimum value located between the lengths $e_3$ and $e_4$ shall not be adopted as a boundary point. In the case of this embodiment, the lengths of $d'_1$, $d'_2$, $d'_3$ and $d'_4$ shown in FIG. 13 may be determined and their ratio of $d'_1:d'_2:d'_3:d'_4$ may be used. In this case, with the sample to be examined shown in FIG. 14, the lengths $e'_1$, $e'_2$, $e'_3$, $e'_4$ and $e'_5$ are determined and the following ratios are determined:

$$e'_2:e'_3:e'_4:e'_5 \qquad (1)$$

$$e'_1{:}e'_3{:}e'_4{:}e'_5 \tag{2}$$

$$e'_1{:}e'_2{:}e'_4{:}e'_5 \tag{3}$$

$$e'_1{:}e'_2{:}e'_3{:}e'_5 \tag{4}$$

$$e'_1{:}e'_2{:}e'_3{:}e'_4 \tag{5}$$

The combination having the value nearest to that of the above described ratio of $d'_1{:}d'_2{:}d'_3{:}d'_4$ may be selected from among these ratios. That is to say, in the case of FIG. 14, the combination in (3) above is found to be the nearest. That is to say, the point on the abscissa x corresponding to the length $e'_3$ is found to be a peak top produced by an abnormal fraction. In which fraction, that is, in which of the fraction between F and H and the fraction between G and I in FIG. 14 the peak located in the position on the abscissa x corresponding to the length $e'_3$ should be included may be determined as follows. In one of the methods, by adopting the above described first conventional method, the concentration of the minimum value located in the position indicated by G and that of the minimum value located in the position indicated by H may be compared with each other and the minimum value lower in the concentration may be made a true boundary point. That is to say, in the example in FIG. 14, G becomes a true boundary point and therefore the peak located in the position on the abscissa x corresponding to the length $e'_3$ is treated as included in the fraction between the positions G and I. There is considered another method wherein the ratio of the concentrations of the fraction between the positions F and H and the fraction between the positions H and I and the ratio of the concentrations of the fraction between the positions F and G and the fraction between the positions G and I are determined and the concentration ratio nearer to the normal ratio of the concentrations, that is, to the ratio of the concentrations of the fraction between the positions F and G and the fraction between the positions G and I in FIG. 13 of the above mentioned concentration ratios is made to be of a normal fraction.

Figure 15:
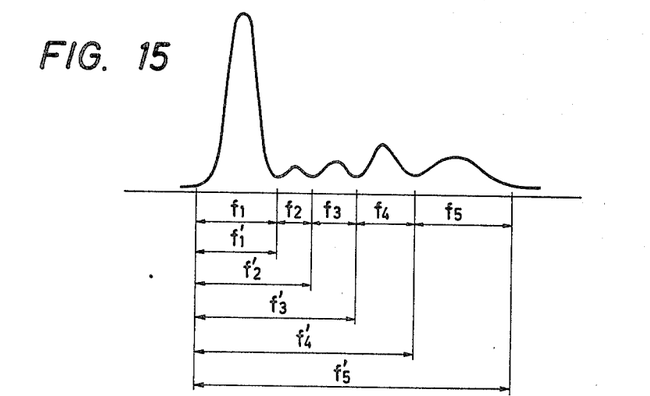
FIG. 15 is an electrophoretic pattern diagram for explaining the third embodiment of the present invention.

FIG. 15 is a diagram for explaining the third embodiment and shows an example that the position of the minimum value is selected as a basic position. This diagram shows an electrophoretic pattern of a standard sample. First the length from the starting point to the point on the abscissa x showing the first minimum value is made $f_1$, the lengths between the respective points on the abscissa x showing the respective minimum values following it are made respectively $f_2$, $f_3$ and $f_4$, the length from the point on the abscissa x showing the last minimum value to the end of the pattern is made $f_5$ and the ratio of $f_1{:}f_2{:}f_3{:}f_4{:}f_5$ is determined. Then, also in the electrophoretic pattern of the sample to be examined, the length from the starting point to the point on the abscissa x showing the first minimum value, the lengths between the points on the abscissa x showing the respective minimum values following it and the length from the point on the abscissa x showing the last minimum value to the end of the pattern are determined, for example, as $k_1$, $k_2$,—(not illustrated). If the electrophoretic pattern of the sample to be examined is such as is shown in FIG. 14, six length sections $k_1$, $k_2$, $k_3$, $k_4$, $k_5$ and $k_6$ will be present. The following ratios are determined in the same manner as in the second embodiment on the basis of the thus determined respective lengths.

$$(k_1+k_2){:}k_3{:}k_4{:}k_5{:}k_6 \tag{1}$$

$$(k_1+k_2){:}k_3{:}k_4{:}k_5{:}k_6 \tag{2}$$

$$(k_1+k_2){:}k_3{:}k_4{:}k_5{:}k_6 \tag{3}$$

$$(k_1+k_2){:}k_3{:}k_4{:}k_5{:}k_6 \tag{4}$$

$$k_1{:}k_2{:}k_3{:}k_4{:}(k_5+k_6) \tag{5}$$

If the combination showing the value of the ratio nearest to the ratio of $f_1{:}f_2{:}f_3{:}f_4{:}f_5$ is determined from among them, it will correspond to a correct fraction and therefore the pattern will be able to be fractionated into five fractions in exactly the same manner as is described above. In the case of this embodiment, too, the ratio of $f'_1{:}f'_2{:}f'_3{:}f'_4{:}f'_5$ is determined from the respective lengths $f'_1$, $f'_2$, $f'_3$, $f'_4$ and $f'_5$ in FIG. 15, then the respective lengths $k'_1$, $k'_2$, $k'_3$, $k'_4$, $k'_5$ and $k'_6$ (not illustrated) corresponding to the sample to be examined and such six ratios as are mentioned below are made from them and are compared with the above mentioned ratio of $f'_1{:}f'_2{:}f'_3{:}f'_4{:}f'_5$ so that the pattern can be fractionated:

$$k'_2{:}k'_3{:}k'_4{:}k'_5{:}k'_6 \tag{1}$$

$$k'_2{:}k'_3{:}k'_4{:}k'_5{:}k'_6 \tag{2}$$

$$k'_2{:}k'_3{:}k'_4{:}k'_5{:}k'_6 \tag{3}$$

$$k'_2{:}k'_3{:}k'_4{:}k'_5{:}k'_6 \tag{4}$$

$$k'_1{:}k'_2{:}k'_3{:}k'_4{:}k'_5 \tag{5}$$

Figure 16:
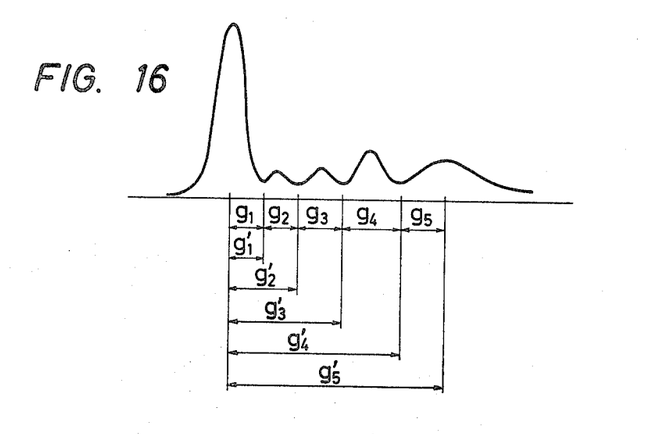
FIG. 16 is an electrophoretic pattern diagram for explaining the fourth embodiment of the present invention.

Further, FIG. 16 is a diagram for explaining the fourth embodiment. In this embodiment, the point on the abscissa x corresponding to the first peak as a basic point, the length $g_1$ from the basic point to the point on the abscissa x showing the first minimum value, the lengths $g_2$, $g_3$ and $g_4$ between the respective points on the abscissa x showing the respective minimum values following it and the length $g_5$ from the point on the abscissa showing the last minimum value to the point on the abscissa x corresponding to the last peak are determined and further the ratio of $g_1{:}g_2{:}g_3{:}g_4{:}g_5$ is determined by using them. Then, with the sample to be examined, too, the same lengths and ratio are determined and the pattern is fractionated by substantially the same method as is used in the second and third embodiments. In this embodiment, too, the pattern can be fractionated in the same manner by using lengths $g'_1$, $g'_2$, $g'_3$, $g'_4$ and $g'_5$ instead of the lengths $g_1$, $g_2$, $g_3$, $g_4$ and $g_5$.

Figure 17:
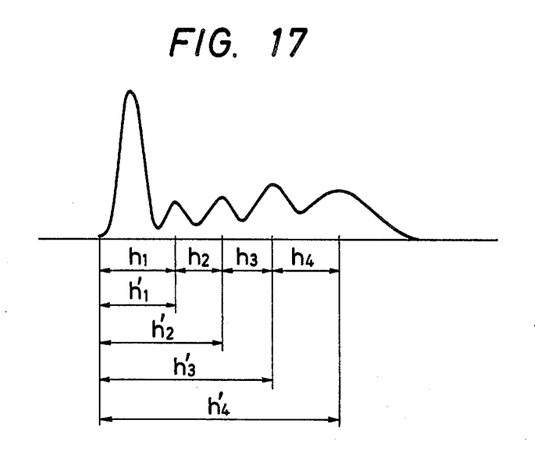
FIG. 17 is an electrophoretic pattern diagram for explaining the fifth embodiment of the present invention.

FIG. 17 is a diagram for explaining the fifth embodiment wherein the starting position in the electrophoretic pattern is made a basic point and the pattern is fractionated on the basis of the lengths between this basic point and the respective points on the abscissa x corresponding to the respective peaks. That is to say, in FIG. 17, the pattern is fractionated by the same method as is used in the second and other embodiments by using the respective lengths $h_1$, $h_2$, $h_3$ and $h_4$ or $h'_1$, $h'_2$, $h'_3$ and $h'_4$.

In the above explanation made with reference to the respective embodiments, the case that the sample to be examined has one abnormal boundary point, that is, five boundary points is described. However, even in the case of two or more abnormal points, that is, six or more boundary points, the pattern will be able to be fractionated in the same manner.

In the case of six boundary points, the length sections $e_1$ to $e_6$ will be present in the second embodiment. Therefore, the following combinations of the ratios of the lengths $e_1$, $e_2$,—$e_6$ may be determined:

$$(e_1+e_2+e_3):e_4:e_5:e_6 \quad (1)$$

$$e_1:(e_2+e_3+e_4):e_5:e_6 \quad (2)$$

$$e_1:(e_2+e_3+e_4):e_5:e_6 \quad (3)$$

$$e_1:(e_2+e_3+e_4):e_5:e_6 \quad (4)$$

$$(e_1+e_2):(e_3+e_4):e_5:e_6 \quad (5)$$

$$e_1:(e_2+e_3):(e_4+e_5):e_6 \quad (6)$$

These combinations are so many that, the more the abnormal boundary points, the more the combinations. However, as described later, the fractionation in the present invention can be made by using a computer and is therefore simple. However, the electrophoretic patterns having abnormal fractions are substantially similar in the form to each other. Therefore, even if the fractionation is limited to the case of six fractions and the next described case of four fractions and is not made in other cases, it will not be influenced. That is to say, for example, a pattern of seven fractions will very rarely appear.

Now, the sample to be examined of an electrophoretic pattern having four fractions shall be explained.

Figure 18:
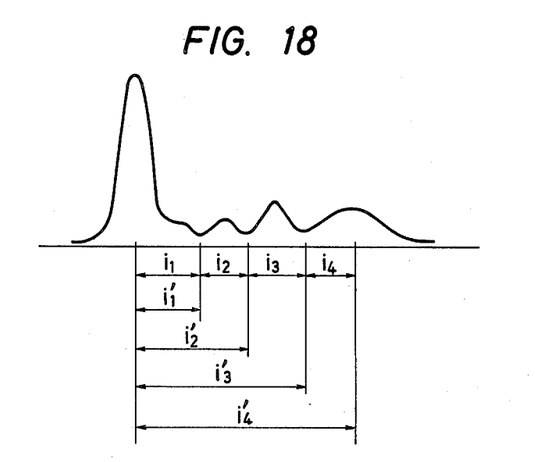
FIG. 18 is an electrophoretic pattern diagram for explaining a method of fractionating an electrophoretic pattern into four fractions.

FIG. 18 shows an example of an electrophoretic pattern of four fractions. In this diagram, $i_1$, $i_2$, $i_3$ and $i_4$ or $i'_1$, $i'_2$, $i'_3$ and $i'_4$ are used as length sections, that is, correspond to $g_1$, $g_2$, $g_3$, $g_4$ and $g_5$ or $g'_1$, $g'_2$, $g'_3$, $g'_4$ and $g'_5$ of the standard sample shown in FIG. 16. In order to thus fractionate the pattern of the sample to be examined, the ratio of $i_1:i_2:i_3:i_4$ is taken by using the length sections $i_1$, $i_2$, $i_3$ and $i_4$ in FIG. 18. On the other hand, the following ratios are taken by using $g_1$, $g_2$, $g_3$, $g_4$ and $g_5$ in FIG. 16 of the standard sample:

$$(g_1+g_2):g_3:g_4:g_5 \quad (1)$$

$$g_1:(g_2+g_3):g_4:g_5 \quad (2)$$

$$g_1:g_2:(g_3+g_4):g_5 \quad (3)$$

$$g_1:g_2:g_3:(g_4+g_5) \quad (4)$$

The above four ratios are compared with the ratio of $i_1:i_2:i_3:i_4$ and the ratio having the nearest value is determined. As evident from the diagram, the ratio in (1) above is the nearest. Therefore, is is found that the boundary point of $g_1$ is not fractionated. Therefore, the boundary point located within the length section $g_1$ in FIG. 16 is added between the basic point and the point on the abscissa x corresponding to the length i from the basic point in the electrophoretic pattern of the sample to be examined shown in FIG. 18 in the fractionation. Thereby, such four fractions as in FIG. 18 can be treated in five correct fractions. Now, the fractionation of the sample to be examined shown in FIG. 18 by using the length sections $i'_1$, $i'_2$, $i'_3$ and $i'_4$ shall be explained. In this case, the following respective ratios are determined by using the length sections $g'_1$, $g'_2$, $g'_3$, $g'_4$ and $g'_5$ shown in FIG. 16:

$$g'_2:g'_3:g'_4:g'_5 \quad (1)$$

$$g'_1:g'_3:g'_4:g'_5 \quad (2)$$

$$g'_1:g'_2:g'_4:g'_5 \quad (3)$$

$$g'_1:g'_2:g'_3:g'_5 \quad (4)$$

$$g'_1:g'_2:g'_3:g'_4 \quad (5)$$

When the combination showing the value nearest to that of the ratio of $i'_1:i'_2:i'_3:i'_4$ is determined from among these ratios, in the case of FIG. 18, the ratio in (1) above will be found to show the nearest value. Therefore, it is found that no boundary point is present within the range of the length section $g_1$. Therefore, if the point on the abscissa x corresponding to the length $g_1$ from the basic point is added as a boundary point, the pattern will be able to fractionated into five correct fractions.

In the method of fractionating the pattern into four fractions, in taking the ratios, those shown in FIG. 16 were used but, even if those in FIGS. 13, 15 and 17 are used, the pattern will be able to be fractionated.

Lastly, the means of automatically working the methods of the above respective embodiments by using a computer shall be briefly explained.

The respective peak points, minimum points and positions on the abscissa x corresponding to them can be easily determined by using the above described first conventional method. As described above, if the kinds of the carriers are the same, the basic ratio of $d_1:d_2:d_3:d_4$ will be fixed. Therefore, the values of the lengths $d_1$, $d_2$, $d_3$ and $d_4$ may be determined in advance for the respective kinds of the carriers and may be memorized in the memory. Further, the values of the length sections $e_1$, $e_2$,— and $e'_1$, $e'_2$,— in the electrophoretic pattern of the sample to be examined may be also determined by determining the peak points and minimum points by using the first conventional method and using the values on the abscissa x corresponding to them and coordinates at fixed time intervals. Further, the comparison of the respective ratios in (1) to (5) below obtained from the sample to be examined, for example, with the basic ratio of $d'_1:d'_2:d'_3:d'_4$ shall be explained:

$$e'_2:e'_3:e'_4:e'_5 \quad (1)$$

$$e'_1:e'_3:e'_4:e'_5 \quad (2)$$

$$e'_1:e'_2:e'_4:e'_5 \quad (3)$$

$$e'_1:e'_2:e'_3:e'_5 \quad (4)$$

$$e'_1:e'_2:e'_3:e'_4 \quad (5)$$

First, on the ratio in (1) above, the minimum value $f_{min}(\alpha_1)$ of $f(\alpha)$ is determined by using the formula $f(\alpha)=(d'_1-\alpha e'_2)+(d'_2-\alpha e'_3)+(d'_3-\alpha e'_4)+(d'_4-\alpha e'_5)+k_1\alpha^2+k_2\alpha+k_3$. In the same manner, on the ratios in (2) to (5) above, the respective minimum values $f_{min}(\alpha_2)$, $f_{min}(\alpha_3)$, $f_{min}(\alpha_4)$ and $f_{min}(\alpha_5)$ are determined. If the smallest one of these values is taken, it will be the nearest to the basic ratio. This calculation can be easily made by a computer.

In the above explanation, FIGS. 13 and 15 show the electrophoretic patterns of the standard sample, but those patterns will not be required to measure in each fractionation. As described above, the values for the respective kinds of the carriers may be determined in advance and may be memorized in the computer.

We claim:

1. A fractionating method in electrophoresis comprising a first step wherein points on an abscissa corresponding to peak tops and minimum points on a densitogram obtained by electrophoresizing a reference human serum sample are determined in advance by scanning the densitogram obtained by electrophoresizing said reference serum sample and are memorized as reference positions, a second step wherein said reference positions are made to correspond so as to have the same basic position on an abscissa of a densitogram obtained by electrophoresizing a human serum sample to be examined, a third step wherein the points on the abscissa corresponding to minimum points on the densitogram obtained by electrophoresizing said human serum sample to be examined are automatically compared with said reference positions corresponding to them and only the points on the abscissa corresponding to the minimum points nearest to said reference positions are treated as boundary points; and a fourth step wherein said reference positions are treated as boundary points when the points on the abscissa corresponding to the minimum points nearest to said reference positions are not present in said third step.

2. A method according to claim 1 wherein said basic position is selected to be the point on the abscissa corresponding to a peak top of an albumin fraction.

3. A method according to claim 1 wherein said basic position is selected to be the point on the abscissa corresponding to the starting position of said densitogram.

4. A method according to claim 1 further comprising, a fifth step wherein ratios of the lengths along the abscissa from said basic position to the respective peak tops or the respective minimum points, the lengths along the abscissa between the adjacent peak tops or between the adjacent minimum points or the lengths obtained by combining these lengths on said densitogram of the human serum sample to be examined are determined, and a sixth step wherein said ratios are compared with reference ratios obtained corresponding to said ratios from said reference positions and said densitogram obtained by electrophoresizing the human serum sample to be examined is fractionated on the basis of the combination of said respective points at which said ratios become to be of the values nearest to those of the reference ratios so as to be of the same number of fractions as the number of fractions on said densitogram of the reference human serum sample.

5. A method according to claim 4 wherein the reference human serum sample is a normal human serum to be examined.

* * * * *